US012670589B2

(12) United States Patent
Takahashi

(10) Patent No.: US 12,670,589 B2
(45) Date of Patent: Jun. 30, 2026

(54) ENDOSCOPIC PHOTOGRAPHIC DEVICE, ENDOSCOPIC PHOTOGRAPHIC METHOD, AND ENDOSCOPIC PHOTOGRAPHIC PROGRAM

(71) Applicant: FUJIFILM Corporation, Tokyo (JP)

(72) Inventor: Azuma Takahashi, Tokyo (JP)

(73) Assignee: FUJILFILM Corporation, Tokyo (JP)

( * ) Notice: Subject to any disclaimer, the term of this patent is extended or adjusted under 35 U.S.C. 154(b) by 365 days.

(21) Appl. No.: 18/296,379

(22) Filed: Apr. 6, 2023

(65) Prior Publication Data

US 2023/0245311 A1      Aug. 3, 2023

Related U.S. Application Data

(63) Continuation of application No. PCT/JP2021/035966, filed on Sep. 29, 2021.

(30) Foreign Application Priority Data

Oct. 12, 2020    (JP) ................................. 2020-172184

(51) Int. Cl.
   *G06K 9/00*        (2022.01)
   *A61B 1/00*        (2006.01)
        (Continued)
(52) U.S. Cl.
   CPC .......... *G06T 7/0012* (2013.01); *A61B 1/0005* (2013.01); *A61B 1/00055* (2013.01);
        (Continued)
(58) Field of Classification Search
   None
   See application file for complete search history.

(56) References Cited

U.S. PATENT DOCUMENTS

2016/0353970 A1    12/2016  Inoue
2018/0160881 A1 *   6/2018  Okabe .................. A61B 1/0004
                (Continued)

FOREIGN PATENT DOCUMENTS

EP          2649931 B1 *  2/2017  ......... A61B 1/00009
WO       2015125592       8/2015
                (Continued)

OTHER PUBLICATIONS

"International Search Report (Form PCT/ISA/210) of PCT/JP2021/035966", mailed on Dec. 14, 2021, with English translation thereof, pp. 1-5.

(Continued)

*Primary Examiner* — Wei Wen Yang
(74) *Attorney, Agent, or Firm* — JCIPRNET

(57) ABSTRACT

A processor acquires an endoscopic image of a subject to be examined that is picked up by an endoscope inserted into a body of the subject to be examined. The processor searches for a similar endoscopic image, which has characteristics similar to characteristics of the acquired endoscopic image, from a plurality of diagnosed endoscopic images with reference to an external device in which the plurality of diagnosed endoscopic images and diagnosis logs about the respective diagnosed endoscopic images including position information indicating a position of a disease are stored. The processor uses the position information, which is included in the diagnosis log about the similar endoscopic image, to specify a photographic position in the subject to be examined at which an image of a disease to be expected in the subject to be examined is capable of being picked up, and notifies of the specified photographic position.

9 Claims, 11 Drawing Sheets

(51) Int. Cl.

| | |
|---|---|
| *A61B 1/045* | (2006.01) |
| *G06T 7/00* | (2017.01) |
| *G16H 30/20* | (2018.01) |
| *G16H 30/40* | (2018.01) |
| *G16H 50/20* | (2018.01) |

(52) U.S. Cl.

CPC ............. *A61B 1/045* (2013.01); *G16H 30/20* (2018.01); *G16H 30/40* (2018.01); *G16H 50/20* (2018.01); *G06T 2207/10068* (2013.01); *G06T 2207/30004* (2013.01)

(56) References Cited

U.S. PATENT DOCUMENTS

| | | | |
|---|---|---|---|
| 2019/0122392 | A1 | 4/2019 | Yamanashi et al. |
| 2019/0282076 | A1* | 9/2019 | Duan .................. A61B 1/0655 |
| 2020/0022560 | A1 | 1/2020 | Oosake |
| 2022/0000338 | A1 | 1/2022 | Saikou |
| 2022/0198742 | A1* | 6/2022 | Nishide .................. G06V 10/82 |

FOREIGN PATENT DOCUMENTS

| | | |
|---|---|---|
| WO | 2017199635 | 11/2017 |
| WO | 2017212725 | 12/2017 |
| WO | 2018180631 | 10/2018 |
| WO | 2019003597 | 1/2019 |
| WO | 2020059377 | 3/2020 |

OTHER PUBLICATIONS

"Written Opinion of the International Searching Authority (Form PCT/ISA/237) of PCT/JP2021/035966", mailed on Dec. 14, 2021, with English translation thereof, pp. 1-6.

"Office Action of Japan Counterpart Application", issued on Feb. 18, 2025, with English translation thereof, p. 1-p. 3.

* cited by examiner

Figure 3:
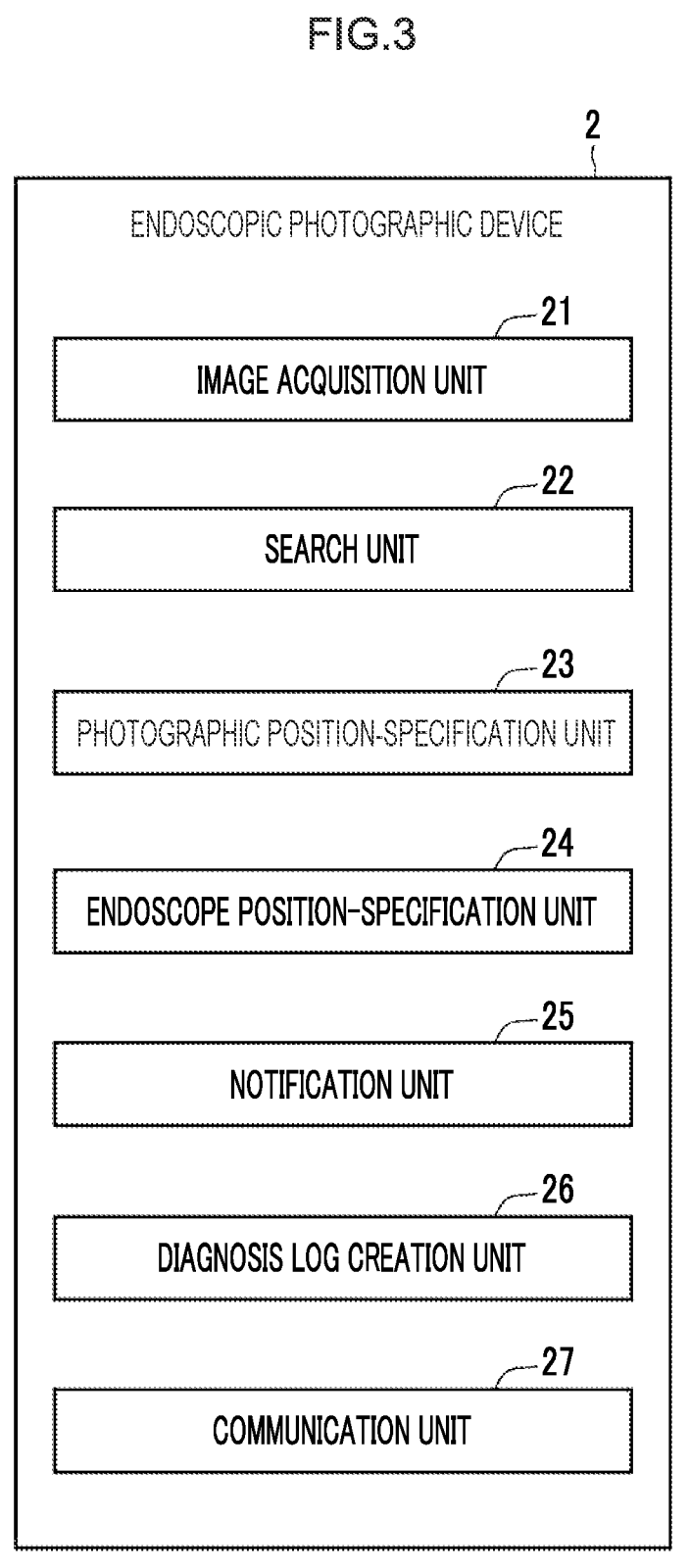

ENDOSCOPIC PHOTOGRAPHIC DEVICE

21

IMAGE ACQUISITION UNIT

22

SEARCH UNIT

23

PHOTOGRAPHIC POSITION-SPECIFICATION UNIT

24

ENDOSCOPE POSITION-SPECIFICATION UNIT

25

NOTIFICATION UNIT

26

DIAGNOSIS LOG CREATION UNIT

27

COMMUNICATION UNIT

35

SIGN OF REFLUX ESOPHAGITIS IS
SEEN IN CARDIA.

GASTRITIS IS SEEN AT LOWER PORTION OF VESTIBULAR PORTION.

GASTRITIS IS SEEN AT LOWER PORTION OF VESTIBULAR PORTION.

GASTRITIS IS SEEN AT LOWER PORTION OF VESTIBULAR PORTION.

2A

ENDOSCOPIC PHOTOGRAPHIC DEVICE

21
IMAGE ACQUISITION UNIT

22
SEARCH UNIT

23
PHOTOGRAPHIC POSITION-SPECIFICATION UNIT

24
ENDOSCOPE POSITION-SPECIFICATION UNIT

25
NOTIFICATION UNIT

26
DIAGNOSIS LOG CREATION UNIT

27
COMMUNICATION UNIT

28
ANALYSIS UNIT

35

GASTRITIS IS RECOGNIZED IN BODY OF STOMACH.
SIGN OF REFLUX ESOPHAGITIS IS SEEN IN CARDIA.

ENDOSCOPIC PHOTOGRAPHIC DEVICE,
ENDOSCOPIC PHOTOGRAPHIC METHOD,
AND ENDOSCOPIC PHOTOGRAPHIC
PROGRAM

CROSS-REFERENCE TO RELATED
APPLICATIONS

The present application is a Continuation of PCT International Application No. PCT/JP2021/035966, filed on Sep. 29, 2021, which claims priority to Japanese Patent Application No. 2020-172184, filed on Oct. 12, 2020. Each application above is hereby expressly incorporated by reference, in its entirety, into the present application.

BACKGROUND

Technical Field

The present disclosure relates to an endoscopic photographic device, an endoscopic photographic method, and an endoscopic photographic program.

Related Art

A similar case search device that searches for a similar case image similar to an image to be diagnosed from a plurality of case images has been proposed. For example, WO2018/180631 and WO2017/199635 propose a method of searching for a similar case that includes an image similar to an image acquired by an endoscopic photographic device and similar disease information.

However, how to utilize the searched similar case for endoscopic photographic and how to improve the accuracy of a diagnosis using an endoscopic image are not proposed in WO2018/180631 and WO2017/199635.

SUMMARY OF THE INVENTION

The present disclosure has been made in consideration of the above-mentioned circumstances, and an object of the present disclosure is to be capable of improving the accuracy of a diagnosis using an endoscopic image by utilizing a similar case about an endoscopic image for endoscopic photograph.

An endoscopic photographic device according to an aspect of the present disclosure comprises at least one processor, and the processor acquires an endoscopic image of a subject to be examined that is picked up by an endoscope inserted into a body of the subject to be examined, searches for a similar endoscopic image, which has characteristics similar to characteristics of the acquired endoscopic image, from a plurality of diagnosed endoscopic images with reference to an external device in which the plurality of diagnosed endoscopic images and diagnosis logs about the respective diagnosed endoscopic images including position information indicating a position of a disease are stored, uses the position information, which is included in the diagnosis log about the similar endoscopic image, to specify a photographic position in the subject to be examined at which an image of a disease to be expected in the subject to be examined is capable of being picked up, and notifies of the specified photographic position.

"Endoscopic image" is a video formed of a plurality of frames. The endoscopic image is acquired from continuous photographing in the subject to be examined, and the number of frames of the endoscopic image is increased with the lapse of time.

"Diagnosed endoscopic image" means an endoscopic image which is provided for a diagnosis and about which a diagnosis log is created.

In the endoscopic photographic device according to the aspect of the present disclosure, the processor may specify a current position of a distal end of the endoscope in the subject to be examined, display an image, which schematically shows an inside of the subject to be examined, and superimpose a position of the distal end of the endoscope and the photographic position on the image schematically showing the inside of the subject to be examined to notify of the photographic position.

Further, in the endoscopic photographic device according to the aspect of the present disclosure, the processor may further notify of an index that indicates a moving direction of the distal end of the endoscope in a case where the distal end of the endoscope is moved into a predetermined range from the photographic position.

Furthermore, in the endoscopic photographic device according to the aspect of the present disclosure, the processor may create a diagnosis log in which an opinion about the acquired endoscopic image is described.

Moreover, in the endoscopic photographic device according to the aspect of the present disclosure, the processor may repeat acquisition of a new endoscopic image at the specified photographic position, search for a new similar endoscopic image based on the new endoscopic image, specification of a new photographic position, and notification of the new photographic position.

Further, in the endoscopic photographic device according to the aspect of the present disclosure, the processor may repeat acquisition of a new endoscopic image at the specified photographic position, search for a new similar endoscopic image based on the new endoscopic image, specification of a new photographic position, notification of the new photographic position, and update of the diagnosis log based on an opinion about the new endoscopic image.

"New endoscopic image" means an endoscopic image added to an endoscopic image acquired up to that point from a predetermined time after the distal end of the endoscope reaches a specific photographic position or before the distal end of the endoscope reaches the specific photographic position.

Furthermore, in the endoscopic photographic device according to the aspect of the present disclosure, the processor may analyze the endoscopic image to detect a disease included in the endoscopic image, and search for the diagnosed endoscopic image, which corresponds to the diagnosis log in which the same disease as the detected disease is described, as the similar endoscopic image.

An endoscopic photographic method according to another aspect of the present disclosure comprises: acquiring an endoscopic image of a subject to be examined that is picked up by an endoscope inserted into a body of the subject to be examined; searching for a similar endoscopic image, which has characteristics similar to characteristics of the acquired endoscopic image, from a plurality of diagnosed endoscopic images with reference to an external device in which the plurality of diagnosed endoscopic images and diagnosis logs about the respective diagnosed endoscopic images including position information indicating a position of a disease are stored; using the position information, which is included in the diagnosis log about the similar endoscopic image, to specify a photographic position in the subject to be examined at which an image of a disease to be expected in the subject to be examined is capable of being picked up; and notifying of the specified photographic position.

The endoscopic photographic method may be provided as a program that causes a computer to perform the endoscopic photographic method according to the other aspect of the present disclosure.

According to the present disclosure, it is possible to improve the accuracy of a diagnosis using an endoscopic image by utilizing a similar case about an endoscopic image for endoscopic photographic.

BRIEF DESCRIPTION OF THE DRAWINGS

FIG. 3 is a diagram showing a functional configuration of the endoscopic photographic device according to the present embodiment.

DETAILED DESCRIPTION

Figure 1:
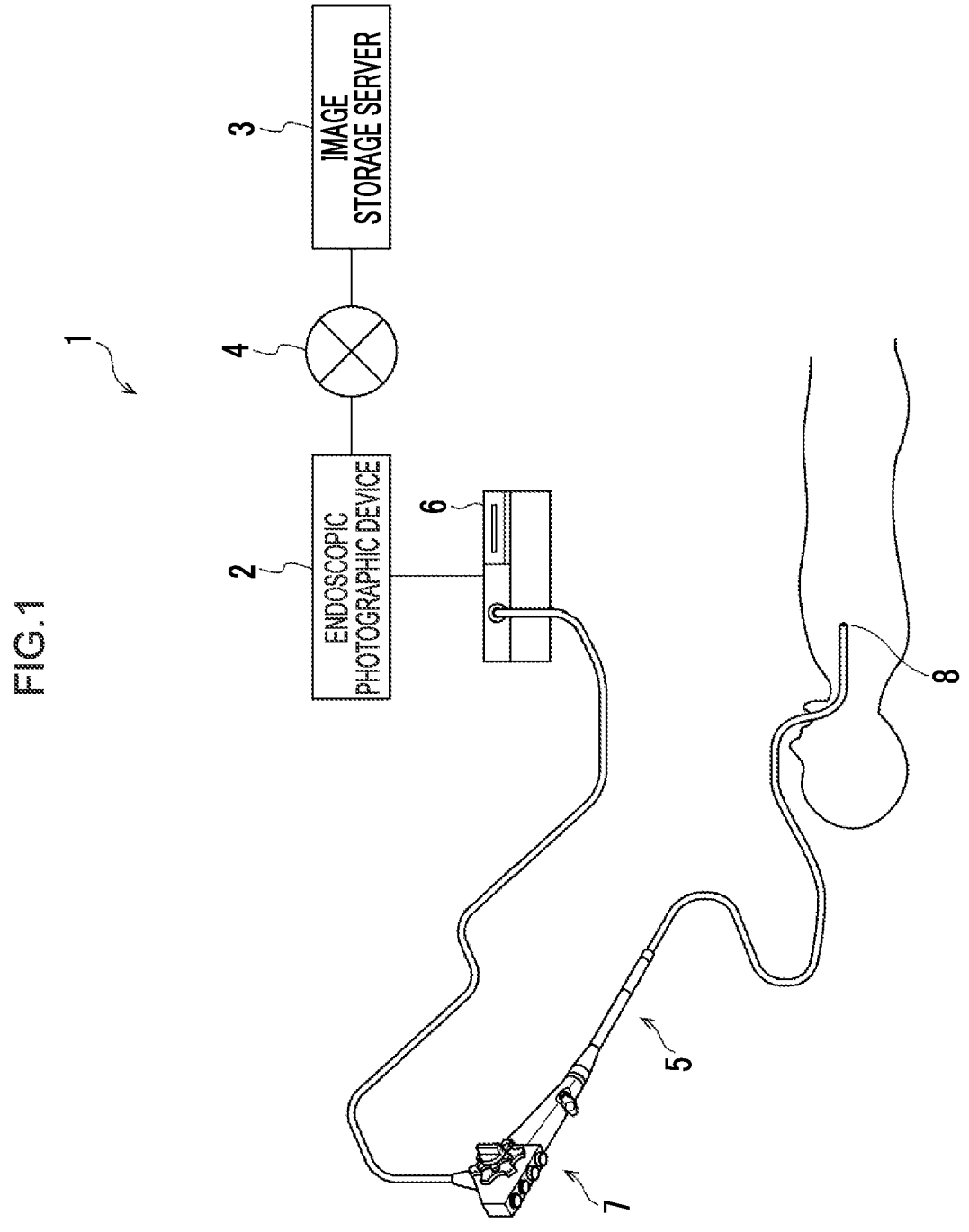
FIG. 1 is a diagram showing a schematic configuration of a medical information system to which an endoscopic photographic device according to an embodiment of the present disclosure is applied.

Embodiments of the present disclosure will be described below with reference to the drawings. FIG. 1 is a hardware configuration diagram showing the outline of a diagnostic support system to which an endoscopic photographic device according to an embodiment of the present disclosure is applied. As shown in FIG. 1, in a diagnostic support system 1, an endoscopic photographic device 2 according to the present embodiment and an image storage server 3 are connected to each other to be capable of communicating with each other via a network 4.

An endoscope 5 that picks up an image of an inside of a subject to be examined and a processor device 6 that generates an image of the inside of the subject to be examined on the basis of signals obtained from the photograph are connected to the endoscopic photographic device 2.

In the endoscope 5, an insertion unit to be inserted into an subject to be examined is continuously mounted on an operation unit 7. The endoscope 5 is connected to the processor device 6 via a universal cord that is attachably and detachably connected to the processor device 6. The operation unit 7 includes various buttons that are used to give an instruction to bend a distal end 8 of the insertion unit in an up-down direction and a left-right direction within a predetermined angular range or to operate a puncture needle mounted on a distal end of the endoscope 5 to collect tissue samples. In the present embodiment, the endoscope 5 is a flexible endoscope for a stomach and is inserted into the stomach through a mouth or a nose of a subject to be examined. Then, light guided by an optical fiber from a light source device (not shown) provided in the processor device 6 is emitted from the distal end 8 of the insertion unit of the endoscope 5, and the image of the inside of the stomach of the subject to be examined is acquired by a photographic optical system of the endoscope 5. In order to facilitate description, the distal end 8 of the insertion unit of the endoscope 5 will be referred to as an endoscope distal end 8 in the following description.

The processor device 6 converts photographic signals captured by the endoscope 5 into digital image signals and corrects image quality using digital signal processing, such as white balance adjustment and shading correction, to generate an endoscopic image T0. Since the generated image is a color video displayed at a predetermined sampling rate, such as 60 fps, the endoscopic image T0 is formed of a plurality of frames. The endoscopic image T0 is sequentially transmitted to the endoscopic photographic device 2 from a generated frame.

The image storage server 3 is a computer that stores and manages various types of data, and comprises a large-capacity external storage device and database management software. The image storage server 3 communicates with the endoscopic photographic device 2 via a wired or wireless network 4, and transmits and receives diagnosis logs and the like using endoscopic images acquired by the endoscopic photographic device 2 and endoscopic images created in the endoscopic photographic device 2. The image storage server 3 stores and manages the received endoscopic images, the received diagnosis logs, and the like in a recording medium, such as a large-capacity storage device. The storage format of the image data of the endoscopic image and the communication between the respective devices via the network 4 are based on a protocol, such as digital imaging and communication in medicine (DICOM). Further, the image storage server 3 is an example of an external device.

The endoscopic images and the diagnosis logs are associated with each other for each examination and are stored in the image storage server 3. Here, the endoscopic image stored in the image storage server 3 is an image which is used for diagnosis and about which a diagnosis log is created. For this reason, in the following description, the endoscopic image acquired in one examination and stored in the image storage server 3 will be referred to as a diagnosed endoscopic image.

An opinion, which is the result of interpretation of the endoscopic image performed by an examiner, is described in a diagnosis log. The opinion includes information, such as the location of a disease recognized in the endoscopic image and the type and size of the disease. For example, in the case of the endoscopic image of the stomach, an opinion including information indicating the names of stomach diseases, such as gastritis, a gastric ulcer, cancer, a polyp, and reflux esophagitis, the position of a disease in a case where the disease is recognized, and the like is described in the diagnosis log. A diagnosis log is created in the endoscopic photographic device 2.

Figure 2:
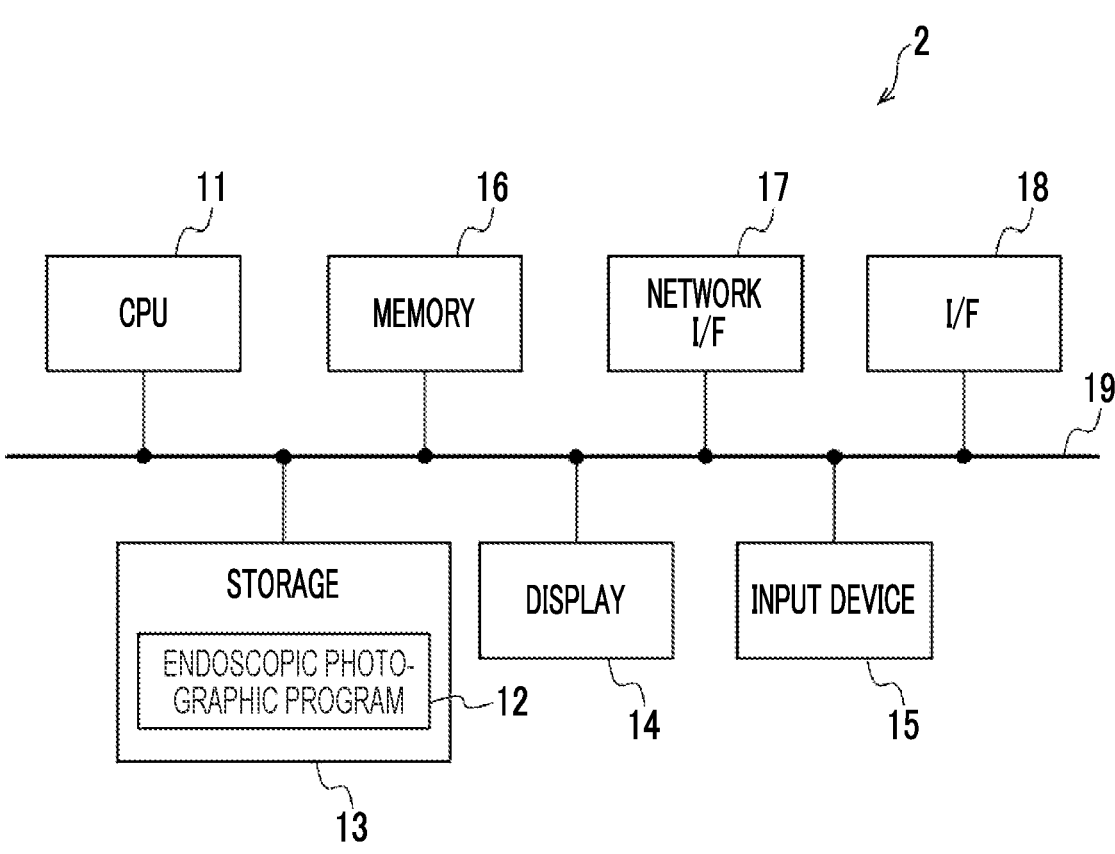
FIG. 2 is a diagram showing a schematic configuration of the endoscopic photographic device according to the present embodiment.

Next, the endoscopic photographic device according to the present embodiment will be described. FIG. 2 illustrates the hardware configuration of the endoscopic photographic device according to the present embodiment. As shown in FIG. 2, the endoscopic photographic device 2 includes a central processing unit (CPU) 11, a non-volatile storage 13, and a memory 16 serving as a temporary storage area. Further, the endoscopic photographic device 2 includes a display 14, such as a liquid crystal display, an input device 15, such as a keyboard and a mouse, a network interface (I/F) 17 that is connected to the network 4, and an I/F 18 that is connected to the processor device 6. The CPU 11, the storage 13, the display 14, the input device 15, the memory 16, the network I/F 17, and the I/F 18 are connected to a bus 19. The CPU 11 is an example of a processor.

The storage 13 is realized by a hard disk drive (HDD), a solid state drive (SSD), a flash memory, and the like. An endoscopic photographic program 12 is stored in the storage 13 serving as a storage medium. The CPU 11 reads out the endoscopic photographic program 12 from the storage 13 and then loads the endoscopic photographic program 12 in the memory 16, and executes the loaded endoscopic photographic program 12.

Next, the functional configuration of the endoscopic photographic device according to the present embodiment will be described. FIG. 3 is a diagram showing a functional configuration of the endoscopic photographic device according to the present embodiment. As shown in FIG. 3, the endoscopic photographic device 2 comprises an image acquisition unit 21, a search unit 22, a photographic position-specification unit 23, an endoscope position-specification unit 24, a notification unit 25, a diagnosis log creation unit 26, and a communication unit 27. Further, in a case where the CPU 11 executes the endoscopic photographic program 12, the CPU 11 functions as the image acquisition unit 21, the search unit 22, the photographic position-specification unit 23, the endoscope position-specification unit 24, the notification unit 25, the diagnosis log creation unit 26, and the communication unit 27.

The image acquisition unit 21 sequentially acquires the respective frames of the endoscopic image T0 transmitted from the processor device 6 via the I/F 18, and stores the frames in the storage 13 as an image file of one endoscopic image T0 in association with an examination ID that is used to specify an examination being currently performed. Here, since the endoscopic image T0 is a video, frames to be acquired are increased with the passage of time. As a result, the size of the image file is also increased. The endoscopic image T0 about the examination being currently performed is referred to as an endoscopic image being diagnosed, and the endoscopic image being diagnosed may be denoted by T0 that is the same reference numeral as the endoscopic image.

Figures 4, 5:
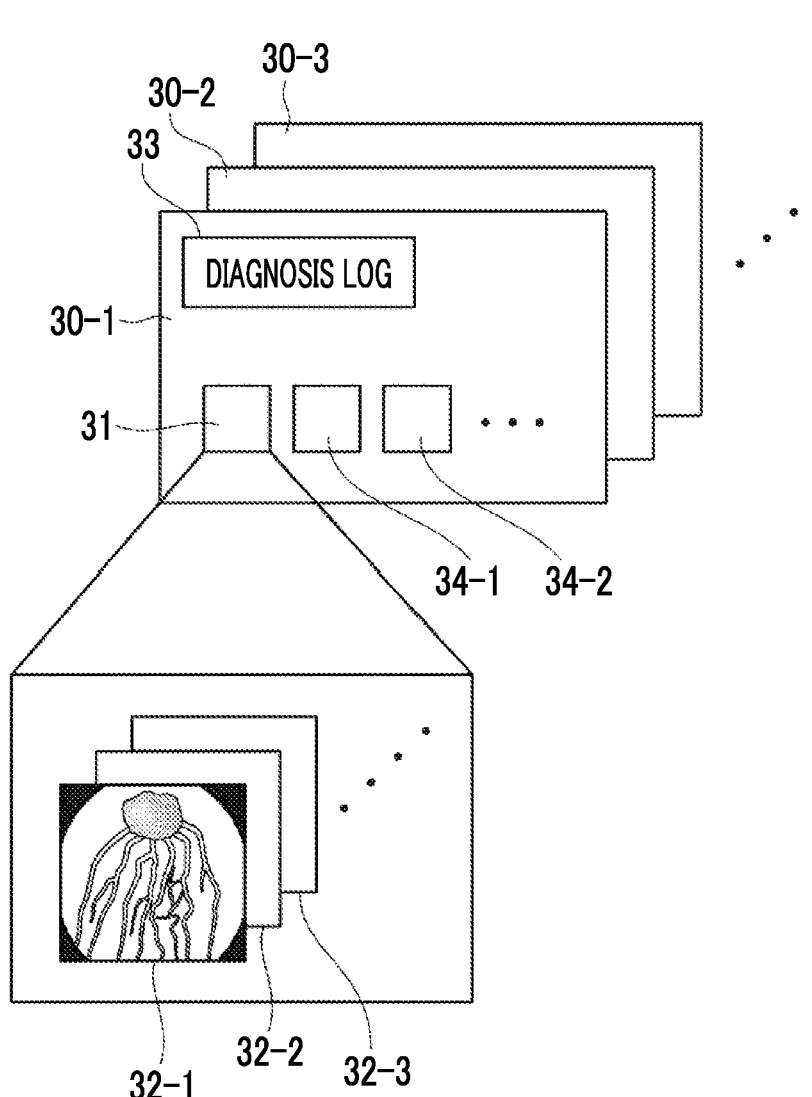
FIG. 4 is a diagram schematically showing a file structure of diagnosed endoscopic images.
FIG. 5 is a diagram showing a diagnosis log about a similar endoscopic image.

The search unit 22 searches for a similar endoscopic image, which has characteristics similar to the characteristics of the endoscopic image T0 being diagnosed acquired by the image acquisition unit 21, from a plurality of diagnosed endoscopic images with reference to the image storage server 3. FIG. 4 is a diagram schematically showing a file structure of the plurality of diagnosed endoscopic images stored in the image storage server 3. As shown in FIG. 4, image files 30-1, 30-2, 30-3, ... of the plurality of diagnosed endoscopic images are stored in the image storage server 3. An endoscopic image 31 as a video acquired in one examination is included in the image file of one diagnosed endoscopic image. Endoscopic images 34-1, 34-2, ... as a plurality of still images may also be included in the image file of one diagnosed endoscopic image. FIG. 4 shows that a plurality of frames 32-1, 32-2, 32-3, ... are included in the endoscopic image 31 serving as a video.

Further, a diagnosis log 33 about the examination is associated with one diagnosed endoscopic image. The diagnosis log 33 is shown in FIG. 4 to be included in each of the image files 30-1, 30-2, 30-3, ... of the diagnosed endoscopic images, but the diagnosis log and the diagnosed endoscopic image may be stored in the image storage server 3 as files separate from each other.

The search unit 22 derives a similarity S1 based on correlation values between the endoscopic image T0 being diagnosed and the plurality of diagnosed endoscopic images. For example, the search unit 22 aligns the latest frame included in the endoscopic image T0 being diagnosed with each of the frames included in the diagnosed endoscopic images, and calculates the absolute value of a difference between pixel values of corresponding pixels of both the frames aligned with each other as the correlation value. Then, the search unit 22 normalizes the correlation values to a value of 0 to 1 and derives the similarity S1. The search unit 22 sorts the diagnosed endoscopic images in order of a frame having a larger similarity S1. Then, the search unit 22 searches for a predetermined number of (one or more) diagnosed endoscopic images having a larger similarity S1 in the sorted diagnosed endoscopic images as the similar endoscopic images.

The photographic position-specification unit 23 refers to diagnosis logs about all the searched similar endoscopic images, and determines whether or not a disease is described in the diagnosis logs. In a case where a disease is not described in the diagnosis logs about all the similar endoscopic images, the photographic position-specification unit 23 waits for the search for the next similar endoscopic image. In a case where there is a similar endoscopic image in which a disease is described in a diagnosis log, the photographic position-specification unit 23 specifies the disease described in the diagnosis log about a similar endoscopic image having the highest similarity and position information indicating the position of the disease. The position information specified in this way indicates a position at which an image of a disease to be expected in an esophagus and stomach of a subject H to be examined under examination can be picked up. The photographic position-specification unit 23 uses the position information of the specified disease to specify a photographic position at which the image of a disease to be expected in the esophagus and stomach of the subject H to be examined can be picked up. The photographic position-specification unit 23 may specify a photographic position in all similar endoscopic images in which a disease and the position of the disease are described in a diagnosis log, on the basis of the most common disease and the position of the disease.

FIG. 5 is a diagram showing a diagnosis log about a certain similar endoscopic image. As shown in FIG. 5, "The sign of reflux esophagitis is seen in the cardia" is described in a diagnosis log 35. In this case, the photographic position-specification unit 23 acquires "reflux esophagitis" as a disease name and information of "cardia" as position information from the diagnosis log 35. For this reason, the occurrence of reflux esophagitis in the cardia is expected from the diagnosis log 35 about the similar endoscopic image.

Figure 6:
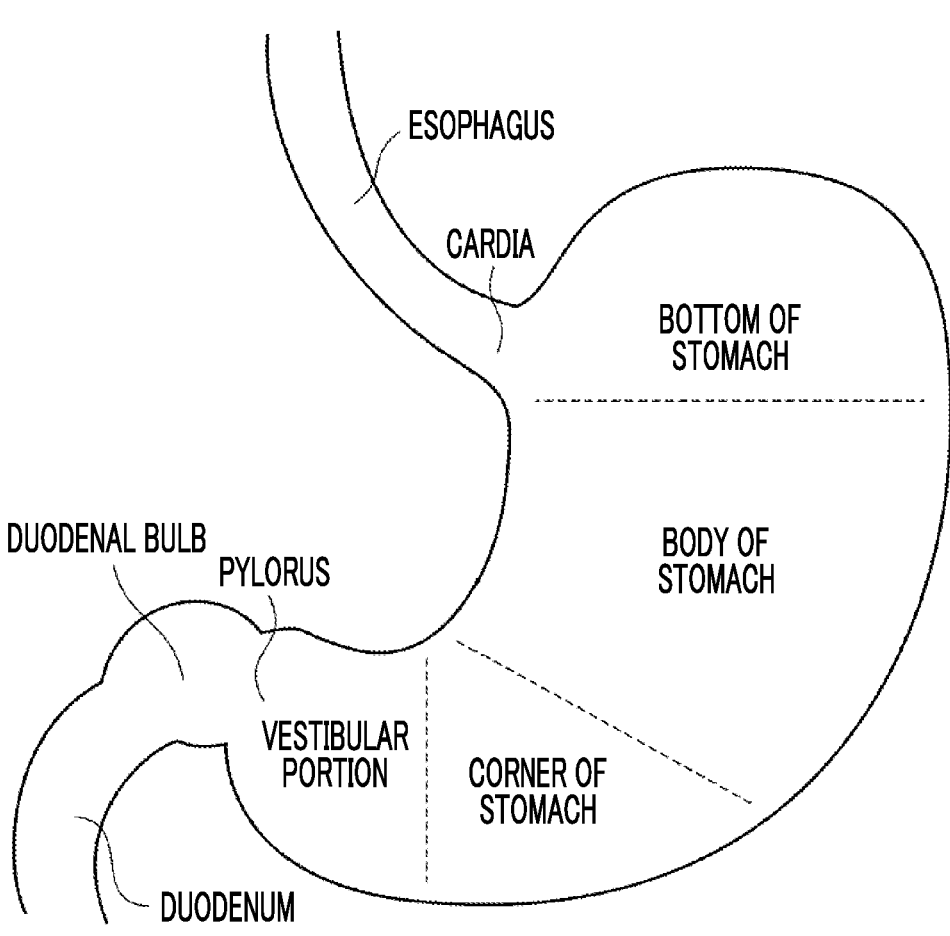
FIG. 6 is a diagram illustrating portions of a stomach.

The endoscope position-specification unit 24 specifies the current position of the endoscope distal end 8. Specifically, the endoscope position-specification unit 24 specifies the current position of the endoscope distal end 8 on the basis of the current frame of the endoscopic image being diagnosed. FIG. 6 is a diagram illustrating portions of a stomach. As shown in FIG. 6, the stomach includes the cardia, the bottom of the stomach, the body of the stomach, the corner of the stomach, the vestibular portion, and the pylorus arranged in order from the esophagus. The endoscope position-specification unit 24 includes a trained model that detects which portion of the stomach a frame indicates in an image, and uses the trained model to detect which portion of the stomach the current frame indicates in an image and to specify the portion of the stomach detected by the trained model as the current position of the endoscope distal end 8. Here, each of the cardia, the bottom of the stomach, the body of the stomach, the corner of the stomach, the vestibular portion, and the pylorus has a characteristic surface structure. For this reason, it is possible to construct a trained model that detects a portion of the stomach included in a frame by causing a neural network to learn while using the image of each of portions of the esophagus and the stomach and the names of the portions as training data.

A method of specifying the current position of the endoscope distal end 8 is not limited to the above-mentioned method. In a case where the endoscope distal end 8 is to be positioned in the stomach, the endoscope distal end 8 necessarily passes through the cardia. For this reason, the moving distance of the endoscope distal end 8 up to the present after the endoscope distal end 8 passes through the cardia may be calculated on the basis of a change in images of frames between the current frame and a frame in which the cardia is detected, and the approximate current position of the endoscope distal end 8 may be specified on the basis of the calculated moving distance. Since the cardia has a characteristic shape, the endoscope position-specification unit 24 detects a frame including the cardia from the endoscopic image being diagnosed. A method using a trained model trained to detect the cardia, a template matching method, or the like can be used for the detection of the frame including the cardia as in the detection of the disease. Alternatively, the endoscope distal end 8 may be provided with an acceleration sensor or a magnetic sensor, and the endoscope distal end 8 may be detected by the sensor.

Figure 7:
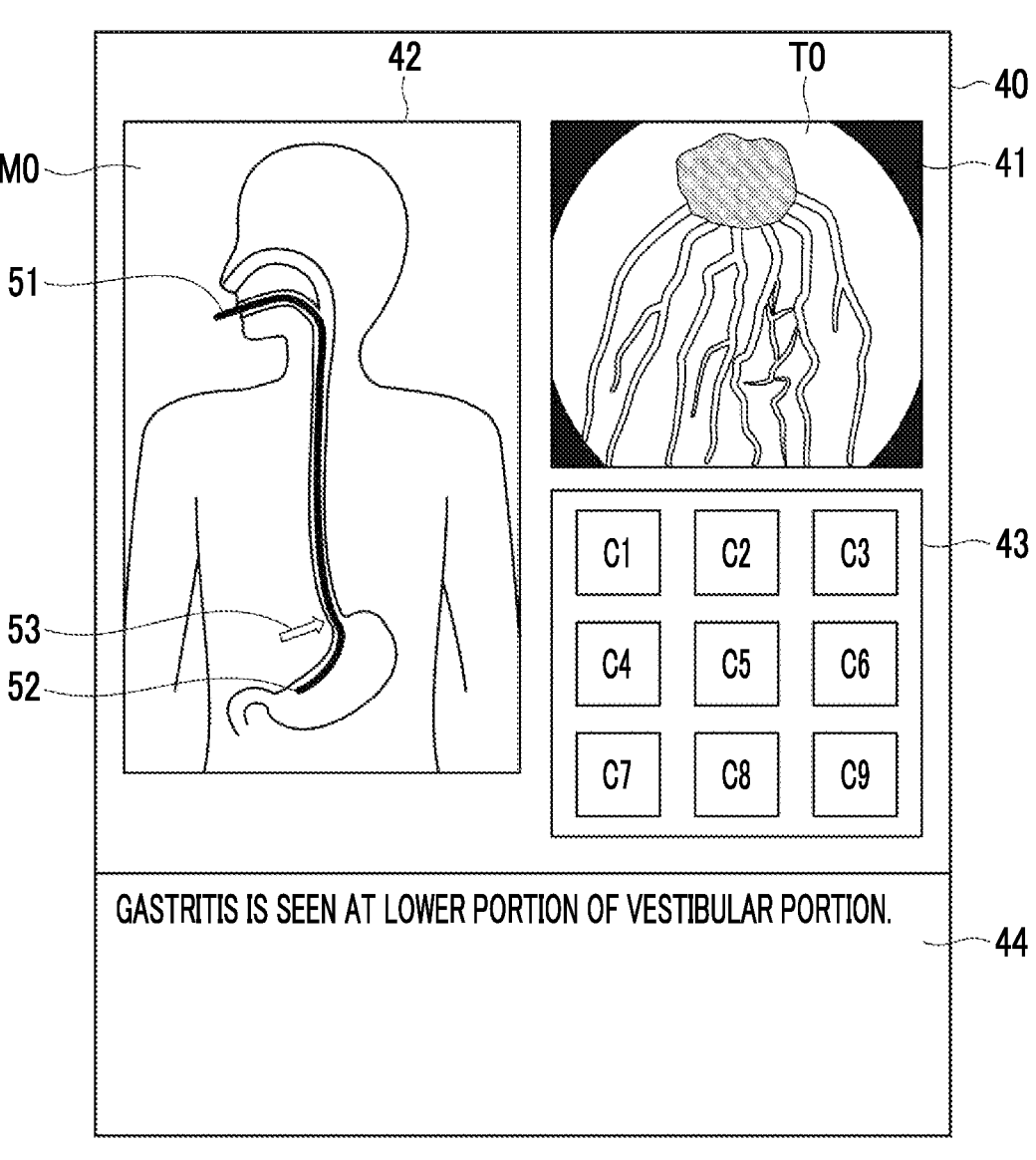
FIG. 7 is a diagram showing a notification screen.

The notification unit 25 notifies the examiner of the photographic position specified by the photographic position-specification unit 23 and the current position of the endoscope distal end 8 specified by the endoscope position-specification unit 24. Specifically, a map image schematically showing the esophagus and stomach of the subject H to be examined is displayed on the display 14, and the current position of the endoscope distal end 8 and the photographic position are superimposed on the displayed map image to notify of the current position of the endoscope distal end 8 and the photographic position. FIG. 7 is a diagram showing a notification screen for the current position of the endoscope distal end 8 and the photographic position. As shown in FIG. 7, the notification screen 40 includes a first image region 41, a second image region 42, and a third image region 43. An endoscopic image T0 being currently picked up is displayed in the first image region 41. A map image M0 is displayed in the second image region 42. Thumbnail images of frames extracted at predetermined time intervals from an endoscopic image T0 acquired after the start of an examination are displayed in the third image region 43.

Nine thumbnail images can be displayed in regions C1 to C9 in the third image region 43. The thumbnail images are displayed in order from the region C1 of the third image region 43 at predetermined time intervals in order after the start of an examination. Then, in a case where a new frame is acquired after the nine thumbnail images are displayed, the thumbnail image of the new frame is displayed in the region C1, the thumbnail images having been displayed up to that point are sent to the regions C2 to C9 in order, and the thumbnail image having been displayed in the region C9 is deleted from the third image region 43.

Further, an opinion region 44 in which the examiner describes an opinion about the endoscopic image T0 is displayed on the notification screen 40. The examiner can input an opinion about the endoscopic image T0 to the opinion region 44 using the input device 15. For example, in a case where a disease of gastritis has already been found in the current examination, an opinion of "Gastritis is seen at the lower portion of the vestibular portion" is described in the opinion region 44.

An endoscope icon 51 schematically showing an endoscope is shown in the map image M0, and the position of a distal end 52 of the endoscope icon 51 is the current position of the endoscope distal end 8. Further, an arrow-shaped mark 53 is superimposed on the photographic position. The photographic position indicates a position near the cardia where reflux esophagitis is suspected. In a case where the examiner refers to the notification screen 40, the examiner can perceive at a glance how the endoscope distal end 8 should be moved to move the endoscope distal end 8 to the photographic position at which a disease is expected.

Figure 8:
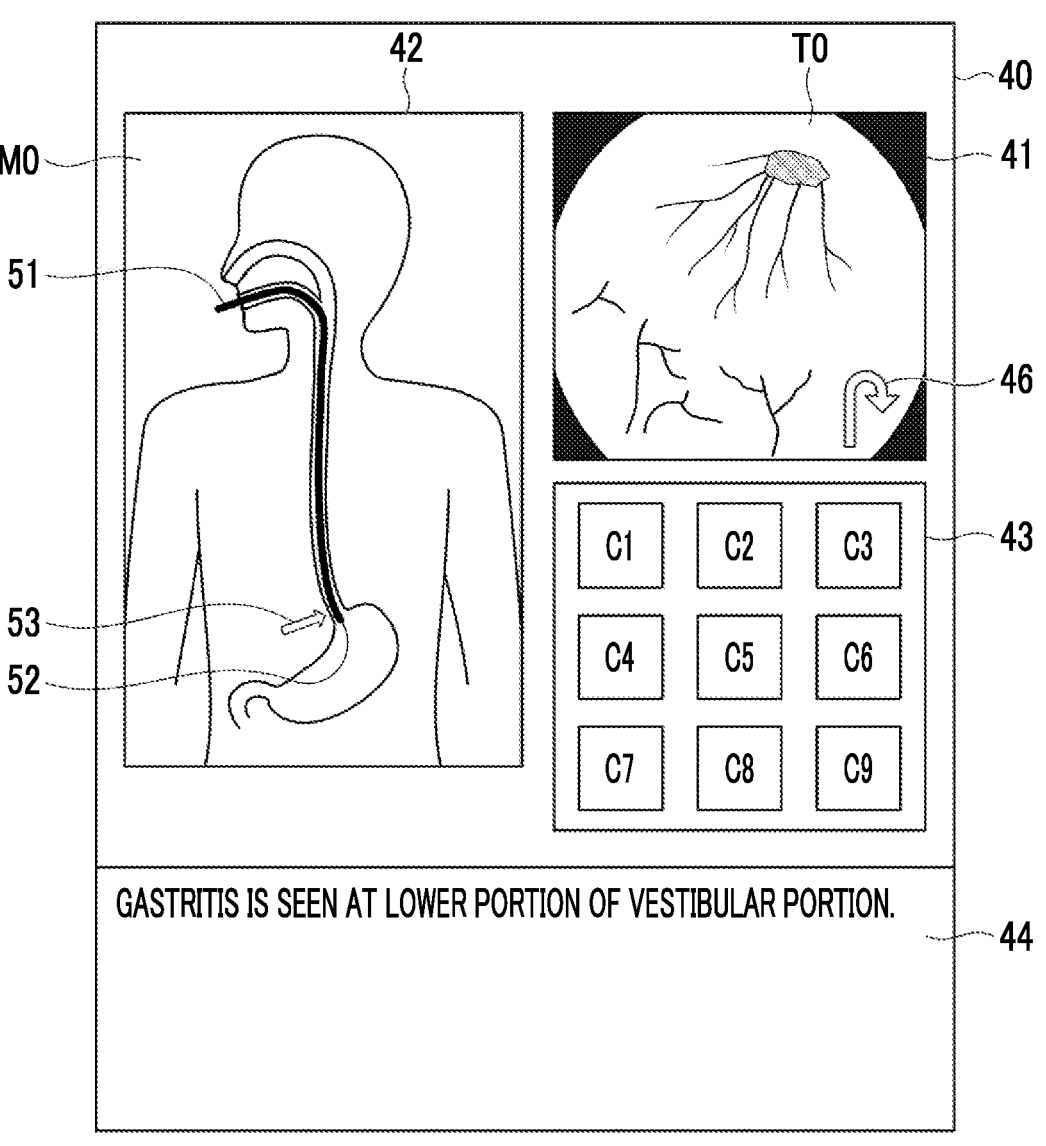
FIG. 8 is a diagram showing a notification screen.

In a case where the endoscope distal end 8 approaches the photographic position at which a disease is expected, the notification unit 25 displays an arrow 46 indicating a direction in which the endoscope distal end 8 is to be moved in the first image region 41 as shown in FIG. 8. The arrow 46 indicates a direction in which the endoscope distal end 8 is moved to return to an esophagus side. Further, it can be seen that the distal end 52 of the endoscope icon 51 is close to the pylorus in the map image M0 as compared to FIG. 7. The arrow 46 is an example of an index indicating the moving direction of the endoscope.

The diagnosis log creation unit 26 describes an opinion, which is input to the opinion region 44 by the examiner, in the diagnosis log to create a diagnosis log. For example, since "Gastritis is seen at the lower portion of the vestibular portion" is already input to FIG. 7 as an opinion, the diagnosis log creation unit 26 describes "Gastritis is seen at the lower portion of the vestibular portion" in a diagnosis log.

In the present embodiment, whenever notification of the photographic position specified by the photographic position-specification unit 23 is sent, photographic is performed at the photographic position and a new endoscopic image is acquired. The new endoscopic image is an endoscopic image that is formed of frames added to the endoscopic image until photographiing is started at the photographic position. For this reason, in the present embodiment, whenever a new endoscopic image is added, the search unit 22 searches for a new similar endoscopic image on the basis of the new endoscopic image. For example, in a case where the examiner moves the endoscope distal end 8 to the photographic position indicated by the mark 53 and a new endoscopic image is acquired, the search unit 22 searches for a new similar endoscopic image using the new endoscopic image, specifically, the latest frame of the new endoscopic image. The search unit 22 may search for a new similar endoscopic image using both a previously acquired endoscopic image and the new endoscopic image. For example, the search unit 22 may search for a similar endoscopic image using the last frame acquired at a previous photographic position and the latest frame.

In this case, the new similar endoscopic image searched for on the basis of the characteristics of the new endoscopic image is highly likely to include an endoscopic image in which a disease different from a disease shown in the previous similar endoscopic image is shown. For this reason, a disease, which is not included in the diagnosis log about the previous similar endoscopic image, is highly likely to be included in a diagnosis log about the new similar endoscopic image. Accordingly, the photographic position-specification unit 23 can specify a new photographic position at which the image of a disease to be expected can be picked up, with reference to the diagnosis log about the new similar endoscopic image. Then, the notification unit 25 notifies of the new photographic position, so that the examiner can move the endoscope distal end 8 to the new photographic position to further acquire a new endoscopic image. The newly acquired endoscopic image is an endoscopic image being diagnosed at the new photographic position.

Figure 9:
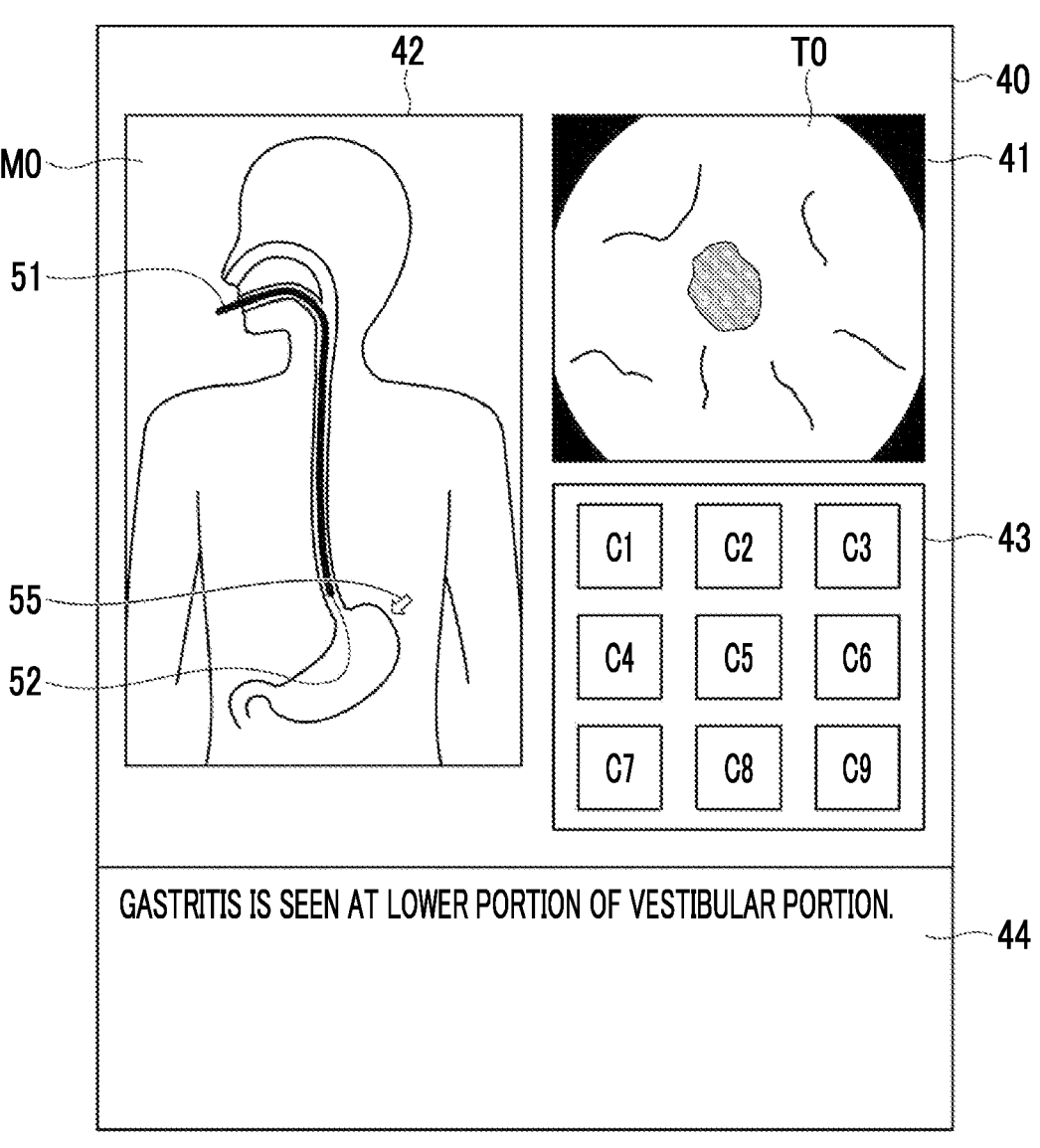
FIG. 9 is a diagram showing a notification screen.

For example, in a case where the examiner moves the endoscope distal end 8 to the photographic position indicated by the mark 53 shown in FIG. 7 to acquire an endoscopic image, it is assumed that the description of a disease about a polyp of the bottom of the stomach is included in the diagnosis log about the searched similar endoscopic image. In this case, the photographic position-specification unit 23 specifies the bottom of the stomach as a photographic position. Accordingly, as shown in FIG. 9, the mark 55 indicating a new photographic position is superimposed on the position of the bottom of the stomach in the map image M0 on the notification screen 40. FIG. 9 shows that the distal end 52 of the endoscope icon 51 is positioned near the cardia. Therefore, it is possible to acquire an endoscopic image at a photographic position at which an image could not be picked up with only the previous similar endoscopic image and to check whether or not a disease occurs.

In a case where an opinion about the new endoscopic image is input to the opinion region 44, the diagnosis log creation unit 26 updates the diagnosis log. For example, in a case where the examiner moves the endoscope distal end 8 to the photographic position indicated by the mark 53 shown in FIG. 7 to acquire a new endoscopic image, the examiner inputs an opinion about the new endoscopic image to the opinion region 44 of the notification screen 40. In a case where an opinion based on the new endoscopic image is input to the opinion region 44, the diagnosis log creation unit 26 adds the input opinion to the diagnosis log to update the diagnosis log.

In a case where an instruction to end an examination is given by the examiner, the communication unit 27 generates an image file of one diagnosed endoscopic image from endoscopic images being diagnosed, which are acquired at a plurality of photographic positions up to that point, and transmits the generated image file to the image storage server 3 together with diagnosis logs described until the end of an examination. The image storage server 3 stores the diagnosed endoscopic image and the diagnosis logs, which are transmitted, as a new diagnosed endoscopic image.

Figure 10:
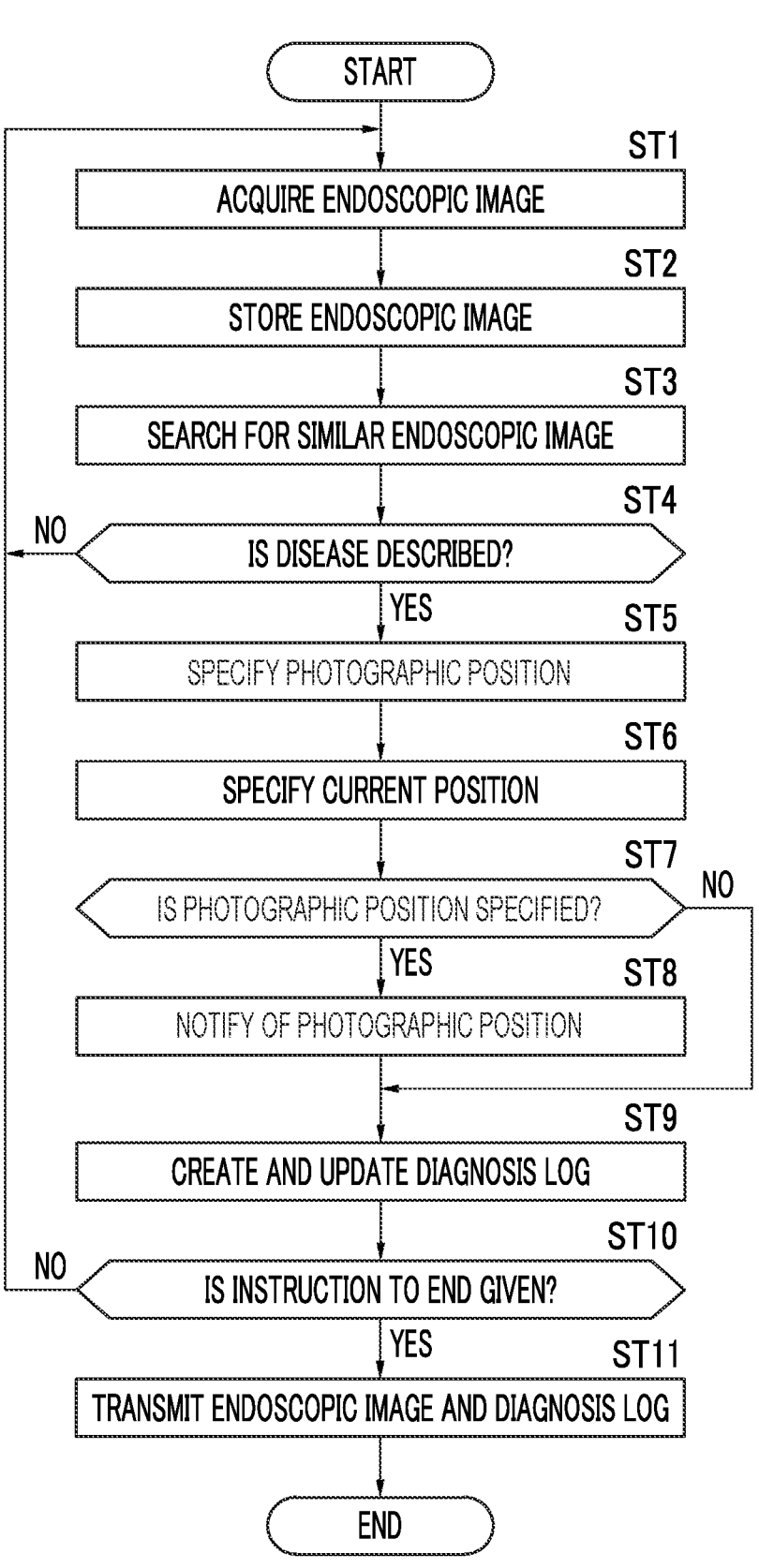
FIG. 10 is a flowchart showing processing that is performed in the present embodiment.

Next, processing performed in the present embodiment will be described. FIG. 10 is a flowchart showing processing that is performed in the present embodiment. An instruction to start an examination is input to start processing, and the image acquisition unit 21 sequentially acquires frames of an endoscopic image T0 (the acquisition of an endoscopic image; Step ST1), and stores the acquired endoscopic image T0 in the storage 13 (Step ST2).

After that, the search unit 22 searches for a similar endoscopic image, which has characteristics similar to the characteristics of the acquired endoscopic image T0, from a plurality of diagnosed endoscopic images with reference to the image storage server 3 (Step ST3). Then, the photographic position-specification unit 23 determines whether or not a disease is described in the diagnosis logs, with reference to the diagnosis log about the similar endoscopic image (Step ST4). In a case where Step ST4 is negative, the processing returns to Step ST1. In a case where Step ST4 is affirmative, the photographic position-specification unit 23 specifies a photographic position in a subject to be examined at which the image of a disease, which is described in a diagnosis log about a similar endoscopic image having the highest similarity and is expected in the subject H to be examined, can be picked up (Step ST5). Further, the endoscope position-specification unit 24 specifies the current position of the endoscope distal end 8 (Step ST6). The processing of Step ST6 may be performed after the processing of any one of Steps ST1 to ST5, or may be performed in parallel with the processing of Steps ST1 to ST5. In a case where the photographic position is specified (Step ST7; affirmative), the notification unit 25 notifies of the specified photographic position (Step ST8).

In a case where Step ST7 is negative and in a case where processing is subsequent to Step ST8, the diagnosis log creation unit 26 receives an opinion input by the examiner and describes the input opinion in the diagnosis log to create a diagnosis log (Step ST9). Subsequently, it is determined whether or not an instruction to end is given (Step ST10). In a case where Step ST10 is negative, the processing returns to Step ST1, and the processing of Steps ST1 to ST10 is repeated. In a case where Step ST10 is affirmative, the communication unit 27 generates an image file of one diagnosed endoscopic image from endoscopic images being diagnosed, which are acquired at the respective specified photographic positions, and transmits the image file of the diagnosed endoscopic image and diagnosis logs to the image storage server 3 (Step ST11), and the processing is ended. In a case where the processing of Steps ST1 to ST10 is repeated, the diagnosis log creation unit 26 updates the diagnosis log in the processing of Step ST9.

As described above, in the present embodiment, a similar endoscopic image having characteristics similar to the characteristics of the endoscopic image being diagnosed is searched for, a photographic position in the body of a subject to be examined at which the image of a disease to be expected in the subject to be examined can be picked up is specified using the position information of a disease included in the diagnosis log about the similar endoscopic image, and notification of the specified photographic position is sent. For this reason, an operator can move the endoscope distal end 8 to the notified of photographic position to acquire an endoscopic image and interpret the acquired endoscopic image to check whether or not a disease is present. Accordingly, it is possible to use a similar endoscopic image to acquire an endoscopic image such that a disease is not overlooked. As a result, it is possible to improve the accuracy of a diagnosis using an endoscopic image.

Further, since the acquisition of a new endoscopic image at a specified photographic position, the search for a new similar endoscopic image based on a new endoscopic image, the specification of a new photographic position, the notification of a new photographic position, and the update of a diagnosis log based on an opinion about a new endoscopic image are repeated, it is possible to acquire an endoscopic image of a subject to be examined at a position at which an image could not be picked up with only the similar endoscopic image and to check whether or not a disease occurs.

Accordingly, it is possible to examine diseases, which are likely to occur, without omission.

Figures 11, 12:
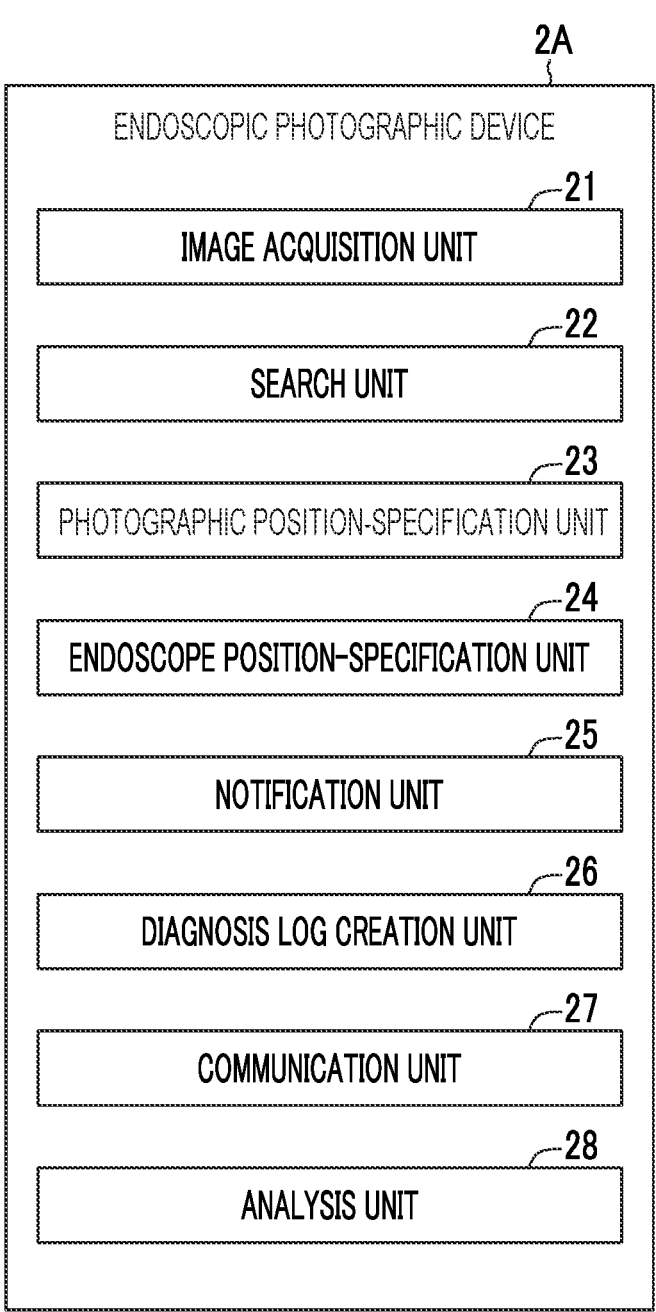
FIG. 11 is a diagram showing a functional configuration of an endoscopic photographic device according to another embodiment.
FIG. 12 is a diagram showing a diagnosis log about a similar endoscopic image.

The endoscopic photographic device according to the present embodiment may include an analysis unit 28 that analyzes an endoscopic image being diagnosed to detect an abnormal shadow from the endoscopic image being diagnosed, as in another endoscopic photographic device 2A according to the present embodiment shown in FIG. 11. The analysis unit 28 sequentially analyzes the respective frames of an endoscopic image T0 being diagnosed to detect diseases included in the endoscopic image T0 being diagnosed. The analysis unit 28 detects a plurality of types of diseases from the endoscopic image T0 being diagnosed using a publicly known computer-assisted image diagnosis (that is, computer-aided diagnosis (CAD)) algorithm. Specifically, in the case of an examination of the stomach, the analysis unit 28 includes a trained model, such as a neural network, having been subjected to machine learning to detect the diseases of the esophagus and the stomach, and detects diseases included in an endoscopic image using the trained model. Examples of the diseases of the esophagus and the stomach include reflux esophagitis, gastritis, gastric ulcer, a polyp, a stomach cancer, and the like. Each of these diseases has a characteristic surface structure. For this reason, it is possible to construct a trained model that detects diseases from an endoscopic image by causing a neural network to learn while using the images of various diseases of the esophagus and the stomach and the types of the diseases as training data.

Instead of the trained model, template matching using a template that shows the shapes of the diseases included in the esophagus, the stomach, and the like may be performed to detect a disease. Further, the analysis unit 28 has only to detect anatomical characteristics from only one frame included in the endoscopic image T0 being diagnosed, particularly, the latest frame, but the detection accuracy for a disease may be low in the case of only one frame. For this reason, the analysis unit 28 may detect a disease from some frames included in the endoscopic image T0 being diagnosed.

In a case where the endoscopic photographic device includes the analysis unit 28 as described above, the search unit 22 may search for a similar endoscopic image corresponding to a diagnosis log in which the same disease as a disease detected from the endoscopic image T0 being diagnosed by the analysis unit 28 is described.

In this case, the photographic position-specification unit 23 determines whether or not the disease name of a disease other than the disease detected from the endoscopic image being diagnosed by the analysis unit 28 is included, with reference to diagnosis logs about all searched similar endoscopic images. In a case where another disease name is included, the description of position information indicating the position of the other disease is included in the diagnosis log. For this reason, in a case where another disease name is included in a diagnosis log about a similar endoscopic image, the photographic position-specification unit 23 acquires the other disease name and the position information thereof from the diagnosis log. In a case where another disease name is not included in the diagnosis logs about all the searched similar endoscopic images, the photographic position-specification unit 23 does not specify a photographic position.

FIG. 12 is a diagram showing a diagnosis log about a certain similar endoscopic image. As shown in FIG. 12, "Gastritis is recognized in the body of the stomach. The sign of reflux esophagitis is seen in the cardia" are described in the diagnosis log 35. Since a disease detected from the endoscopic image being diagnosed by the analysis unit 28 is gastritis, the photographic position-specification unit 23 acquires "reflux esophagitis" as another disease name and information of "cardia" as position information from the diagnosis log 35 in this case. For this reason, the occurrence of reflux esophagitis is expected in the cardia in the subject H to be examined from the diagnosis log 35 about the similar endoscopic image.

Figure 13:
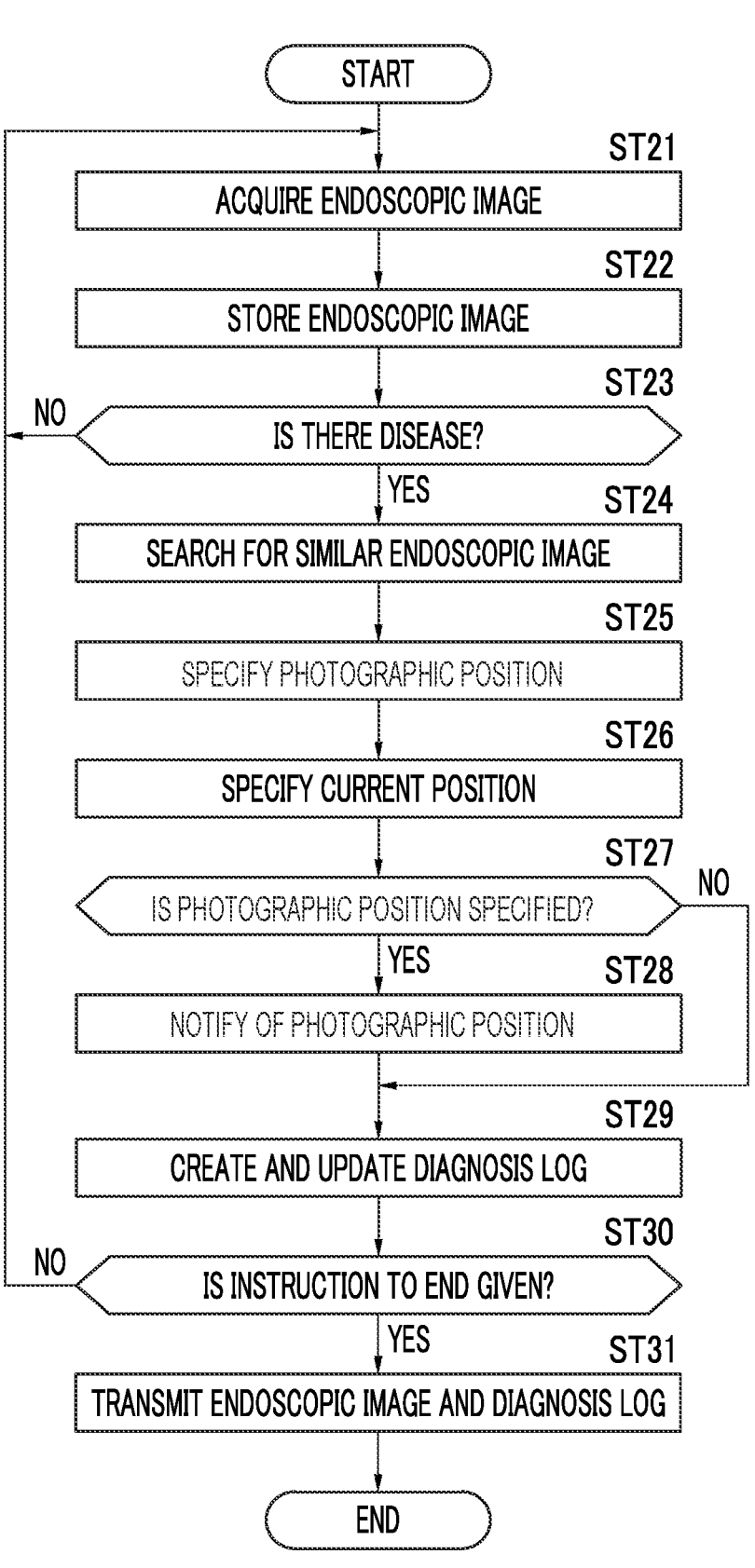
FIG. 13 is a flowchart showing processing that is performed in the other embodiment.

Next, processing performed in another embodiment will be described. FIG. 13 is a flowchart showing processing that is performed in the other embodiment. An instruction to start an examination is input to start processing, and the image acquisition unit 21 sequentially acquires frames of an endoscopic image T0 (the acquisition of an endoscopic image; Step ST21), and stores the acquired endoscopic image T0 in the storage 13 (Step ST22).

After that, the analysis unit 28 analyzes the endoscopic image T0 and determines whether or not a disease is included in the endoscopic image T0 (Step ST23). In a case where Step ST23 is negative, the processing returns to Step ST21. In a case where Step ST23 is affirmative, the search unit 22 searches for a similar endoscopic image, which has characteristics similar to the characteristics of the acquired endoscopic image T0, from a plurality of diagnosed endoscopic images with reference to the image storage server 3 (Step ST24). Then, the photographic position-specification unit 23 specifies a photographic position on the body surface of a subject to be examined at which the image of a disease, which is expected in the subject to be examined, can be picked up, using the diagnosis log about the similar endoscopic image (Step ST25). Further, the endoscope position-specification unit 24 specifies the current position of the endoscope distal end 8 (Step ST26). The processing of Step ST26 may be performed after the processing of any one of Steps ST21 to ST25, or may be performed in parallel with the processing of Steps ST21 to ST25. In a case where the photographic position is specified (Step ST27; affirmative), the notification unit 25 notifies of the specified photographic position (Step ST28).

In a case where Step ST27 is negative and in a case where processing is subsequent to Step ST28, the diagnosis log creation unit 26 receives an opinion input by the examiner and describes the input opinion in the diagnosis log to create a diagnosis log (Step ST29). Subsequently, it is determined whether or not an instruction to end is given (Step ST30). In a case where Step ST30 is negative, the processing returns to Step ST21, and the processing of Steps ST21 to ST30 is repeated. In a case where Step ST30 is affirmative, the communication unit 27 generates an image file of one diagnosed endoscopic image from endoscopic images being diagnosed, which are acquired at the respective specified photographic positions, and transmits the image file of the diagnosed endoscopic image and diagnosis logs to the image storage server 3 (Step ST31), and the processing is ended. In a case where the processing of Steps ST21 to ST30 is repeated, the diagnosis log creation unit 26 updates the diagnosis log in the processing of Step ST29.

In a case where thumbnail images are displayed in the third image region 43 of the notification screen 40 in the other embodiment, a thumbnail image in which a disease is detected may be highlighted. Examples of highlighting include adding a frame to the thumbnail image and adding a mark to the thumbnail image. Further, in a case where the highlighted thumbnail image is double-clicked, a frame of the endoscopic image corresponding to the thumbnail image may be enlarged and displayed in a separate window.

Furthermore, portions of which images are picked up by the endoscopic photographic device 2 are set to the esophagus and the stomach in the above-mentioned embodiments, but are not limited thereto. It is natural that a bronchus and a large intestine may be set as an object to be subjected to photograph.

In each of the above-mentioned embodiments, various processors to be described below can be used as the hardware structures of processing units, which perform various types of processing, such as the image acquisition unit 21, the search unit 22, the photographic position-specification unit 23, the endoscope position-specification unit 24, the notification unit 25, the diagnosis log creation unit 26, the communication unit 27, and the analysis unit 28. The various processors described above include a programmable logic device (PLD) that is a processor of which the circuit configuration can be changed after manufacture, such as a field programmable gate array (FPGA), a dedicated electrical circuit that is a processor having a circuit configuration designed exclusively to perform specific processing, such as an application specific integrated circuit (ASIC), and the like in addition to a CPU that is a general-purpose processor functioning as various processing units by executing software (programs) as described above.

One processing unit may be formed of one of these various processors, or may be formed of a combination of two or more processors of the same type or different types (for example, a combination of a plurality of FPGAs or a combination of a CPU and an FPGA). Further, a plurality of processing units may be formed of one processor.

As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor realizing the functions of the entire system, which includes a plurality of processing units, via one integrated circuit (IC) chip as typified by a system on chip (SoC) or the like is used. In this way, various processing units are formed using one or more of the above-mentioned various processors as hardware structures.

In addition, more specifically, electrical circuitry where circuit elements, such as semiconductor elements, are combined can be used as the hardware structures of these various processors.

What is claimed is:

1. An endoscopic photographic device comprising at least one processor,
wherein the processor
acquires an endoscopic image of a subject to be examined that is picked up by an endoscope inserted into a body of the subject to be examined,
searches for a similar endoscopic image, which has characteristics similar to characteristics of the acquired endoscopic image, from a plurality of diagnosed endoscopic images based on the characteristics of the acquired endoscopic image with reference to an external device in which the plurality of diagnosed endoscopic images and diagnosis logs about the respective diagnosed endoscopic images are stored, wherein position information indicating a position of a disease is included in a diagnosis log about the similar endoscopic image,
refers to the diagnosis log about the similar endoscopic image to specify the position information indicating the position of the disease,

uses the position information to specify a photographic position in the subject to be examined at which an image of the disease to be expected in the subject to be examined is picked up based on the position of the disease indicated by the position information, and
notifies of the specified photographic position for guiding movement of the endoscope.

2. The endoscopic photographic device according to claim 1,
wherein the processor specifies a current position of a distal end of the endoscope in the subject to be examined,
displays an image, which schematically shows an inside of the subject to be examined, and
superimposes a position of the distal end of the endoscope and the photographic position on the image schematically showing the inside of the subject to be examined to notify of the photographic position.

3. The endoscopic photographic device according to claim 2,
wherein the processor further notifies of an index that indicates a moving direction of the distal end of the endoscope in a case where the distal end of the endoscope is moved into a predetermined range from the photographic position.

4. The endoscopic photographic device according to claim 1,
wherein the processor creates a diagnosis log in which an opinion about the acquired endoscopic image is described.

5. The endoscopic photographic device according to claim 1,
wherein the processor repeats acquisition of a new endoscopic image at the specified photographic position, search for a new similar endoscopic image based on the new endoscopic image, specification of a new photographic position, and notification of the new photographic position.

6. The endoscopic photographic device according to claim 4,
wherein the processor repeats acquisition of a new endoscopic image at the specified photographic position, search for a new similar endoscopic image based on the new endoscopic image, specification of a new photographic position, notification of the new photographic position, and update of the diagnosis log based on an opinion about the new endoscopic image.

7. The endoscopic photographic device according to claim 1,
wherein the processor analyzes the endoscopic image to detect a disease included in the endoscopic image, and
searches for the diagnosed endoscopic image, which corresponds to the diagnosis log in which the same disease as the detected disease is described, as the similar endoscopic image.

8. An endoscopic photographic method comprising:
acquiring an endoscopic image of a subject to be examined that is picked up by an endoscope inserted into a body of the subject to be examined;
searching for a similar endoscopic image, which has characteristics similar to characteristics of the acquired endoscopic image, from a plurality of diagnosed endoscopic images based on the characteristics of the acquired endoscopic image with reference to an external device in which the plurality of diagnosed endoscopic images and diagnosis logs about the respective diagnosed endoscopic images are stored, wherein position information indicating a position of a disease is included in a diagnosis log about the similar endoscopic image;

referring to the diagnosis log about the similar endoscopic image to specify the position information indicating the position of the disease;

using the position information to specify a photographic position in the subject to be examined at which an image of the disease to be expected in the subject to be examined is picked up based on the position of the disease indicated by the position information; and notifying of the specified photographic position for guiding movement of the endoscope.

9. A non-transitory computer-readable storage medium that stores an endoscopic photographic program causing a computer to perform a step of acquiring an endoscopic image of a subject to be examined that is picked up by an endoscope inserted into a body of the subject to be examined;

a step of searching for a similar endoscopic image, which has characteristics similar to characteristics of the acquired endoscopic image, from a plurality of diagnosed endoscopic images based on the characteristics of the acquired endoscopic image with reference to an external device in which the plurality of diagnosed endoscopic images and diagnosis logs about the respective diagnosed endoscopic images are stored, wherein position information indicating a position of a disease is included in a diagnosis log about the similar endoscopic image;

a step of referring to the diagnosis log about the similar endoscopic image to specify the position information indicating the position of the disease;

a step of using the position information to specify a photographic position in the subject to be examined at which an image of the disease to be expected in the subject to be examined is picked up based on the position of the disease indicated by the position information; and a step of notifying of the specified photographic position for guiding movement of the endoscope.

* * * * *